United States Patent

Hara et al.

[11] Patent Number: 5,312,334
[45] Date of Patent: May 17, 1994

[54] PERISTALTIC PUMP APPARATUS HAVING AN IMPROVED MISLOADED IV TUBE DETECTING CIRCUIT

[75] Inventors: Keita Hara, Kashihara, Japan; Alan G. Bettisch, Buffalo Grove, Ill.; Joseph B. Matthews, Grayslake, Ill.; Thomas Callaghan, Algonquin, Ill.

[73] Assignee: Sharp Kabushiki Kaisha, Osaka, Japan

[21] Appl. No.: 1,112

[22] Filed: Jan. 5, 1993

[30] Foreign Application Priority Data

Jan. 6, 1992 [JP] Japan .................................. 4-000173

[51] Int. Cl.⁵ .............................................. A61M 31/00
[52] U.S. Cl. ......................................... 604/65; 604/67; 128/DIG. 13
[58] Field of Search .................................. 604/65-67; 128/DIG. 12, DIG. 13

[56] References Cited

U.S. PATENT DOCUMENTS

| | | |
|---|---|---|
| 4,174,637 | 11/1979 | Mulzet et al. |
| 4,460,358 | 7/1984 | Somerville et al. ......... 128/DIG. 13 |
| 4,534,756 | 8/1985 | Nelson ................... 604/65 |
| 4,563,179 | 1/1986 | Sakai .................... 604/67 |
| 4,731,057 | 3/1988 | Tanaka et al. ............ 604/67 |
| 4,797,655 | 1/1989 | Orndal et al. ............ 604/67 |
| 4,838,865 | 6/1989 | Flank et al. ............. 604/65 |
| 4,857,050 | 8/1989 | Lentz et al. ........... 128/DIG. 13 |
| 4,863,425 | 9/1989 | Slate et al. ............. 604/65 |
| 4,884,065 | 11/1989 | Crouse et al. .......... 128/DIG. 13 |
| 4,898,576 | 2/1990 | Philip ................... 604/65 |
| 5,026,348 | 6/1991 | Venegas ................. 604/65 |
| 5,098,380 | 3/1992 | Aizawa et al. ........... 604/67 |
| 5,120,096 | 6/1992 | D'Silva ................. 604/153 |

FOREIGN PATENT DOCUMENTS

| | | |
|---|---|---|
| 0346548 | 12/1989 | European Pat. Off. |
| 0447985A1 | 9/1991 | European Pat. Off. |
| 56-45616 | 2/1981 | Japan . |
| 1-90548 | 4/1989 | Japan . |
| 6443937 | 4/1989 | Japan . |
| 604741 | 9/1978 | Switzerland . |

Primary Examiner—John D. Yasko
Assistant Examiner—Michael Rafa
Attorney, Agent, or Firm—David G. Conlin; George W. Neuner

[57] ABSTRACT

A peristaltic pumping apparatus has a misloaded-tube detector. The detector is constituted of a pair of pressure sensors and a CPU. The pressure sensors are located on both sides of a fluid propelling portion onto which an IV tube containing a solution is loaded. The detector detects a tube misloading by making use of pressure which is applied to one pressure sensor when the tube is displaced onto the pressure sensor and is forced against it by the closing of a door. Each sensor consists of first and second electrodes spaced from each other, a pressure-resistive conductive element attached to the first electrode and spaced from the second electrode and capable of connecting thereto, and a resistor connected to the first and second electrodes. The CPU judges from a resistance value of the pressure sensor as to whether the tube is properly loaded or misloaded or whether the pressure sensor is in an operative state.

5 Claims, 7 Drawing Sheets

Fig. 8A
Fig. 8B
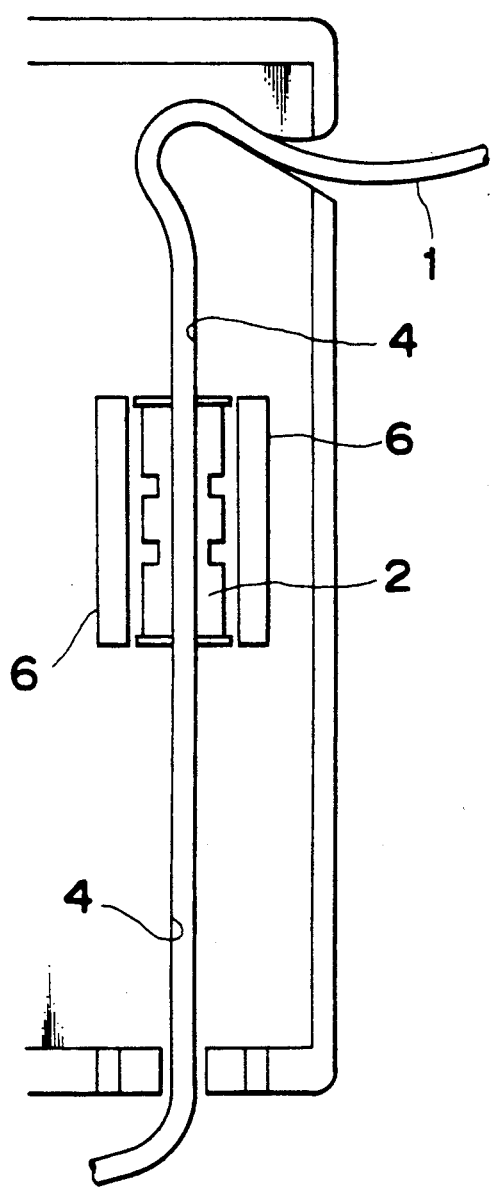
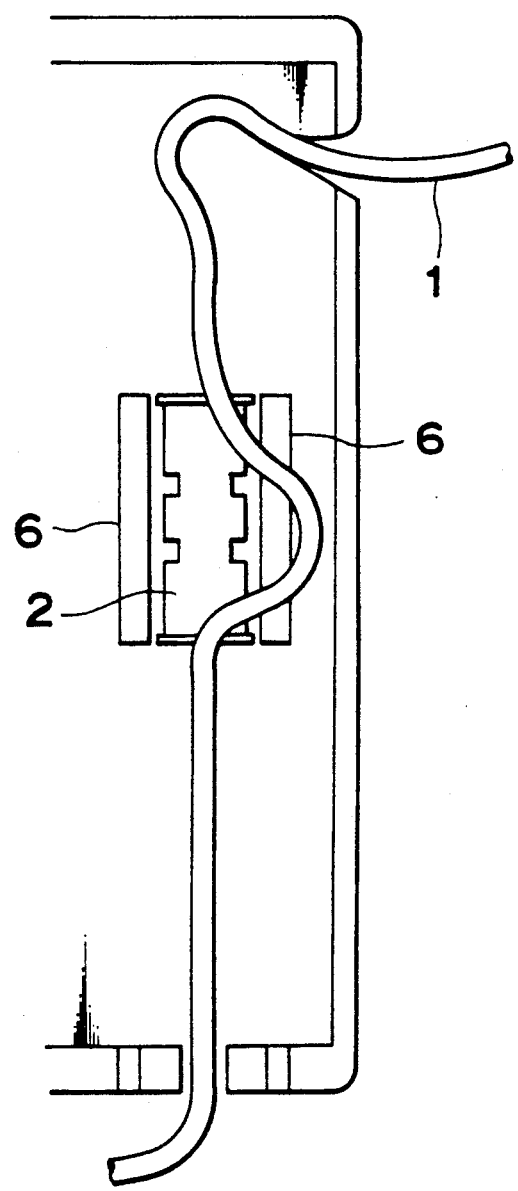

PERISTALTIC PUMP APPARATUS HAVING AN IMPROVED MISLOADED IV TUBE DETECTING CIRCUIT

BACKGROUND OF THE INVENTION

1. Field of the Invention

The present invention generally relates to a peristaltic pumping apparatus and particularly, to a misloaded IV (intravenous) tube detecting circuit for a peristaltic intravenous infusion pump.

2. Description of the Prior Art

Administration of intravenous solutions to a patient is well known in the art. Typically, a solution such as saline, glucose or electrolyte in a glass or flexible container is fed to a patient's venous access site via a length of flexible plastic tubing such as polyvinyl chloride (PVC) tubing. The rate of flow of the solution is controlled by a roller clamp which is adjusted to restrict the flow lumen of the tubing until the desired flow rate is obtained.

Flow from the container to the patient may also be regulated by means other than a roller clamp. It is becoming more and more common to use an electronically controlled pump. One type of pump that is used for intravenous solution administration is a peristaltic-type pump.

Use of peristaltic pumping action is particularly well suited for the medical field. This is because peristaltic pumping action can be applied externally of the tubing carrying the intravenous solution. This maintains the sterile condition of the intravenous solution within the tubing while imparting fluid propulsion on the solution. The peristaltic pumping action can also be applied on any point on the tubing.

In a common type of peristaltic pump used in the medical field, a driving motor is connected to an array of cams which are angularly spaced from each other. The cams in turn drive cam followers which are connected to corresponding pressure fingers. These elements cooperate to impart a linear wave motion on the pressure fingers. A pressure plate is secured juxtaposed to and spaced from the pressure fingers. The pressure plate holds the tubing against the reciprocating pressure fingers to impart the wave motion on the tubing to propel the solution.

In another common type of peristaltic pump used in the medical field, a driving motor is connected via an armature to at least one roller member. The driving motor imparts a circular rotation on the armature which has adapted in the roller member. A semicircular pressure plate having the same center point as the armature is provided with the tubing located between the roller member and the pressure plate. The pressure plate holds the tubing against the roller member which imparts a circular motion on the tubing to propel the solution.

The pump also includes a door mounted on the supporting structure for movement between an open position which allows access to the pumping hardware and a closed position which impedes access to the pumping hardware.

FIG. 7 is a perspective view of a conventional peristaltic intravenous infusion pump in a state that its door is open. As shown in FIG. 7, a wall 3 of a pump body has a fluid propelling portion 2 for executing a peristaltic pumping action and grooves 4 which are respectively leading to and leading from the fluid propelling portion 2. An IV tube 1 is loaded into the groove 4 so that a portion of the IV tube 1 is located on the fluid propelling portion 2. The fluid propelling portion 2 includes pressure fingers as previously described although not illustrated in detail. The door 5 carries a pressure plate 7 associated with the pressure fingers. When the fluid propelling portion 2 is activated after the door 5 has been closed, the fluid propelling portion 2 feeds a solution in the IV tube 1 with a peristaltic pumping action by the reciprocating pressure fingers urging the tube 1 against the pressure plate 7.

Pressure sensors 6 are provided on both sides of the fluid propelling portion 2 to detect misloading of the IV tube 1. FIGS. 9A and 9B show a structure of the pressure sensor 6. Each pressure sensor 6 is comprised of a first electrode 10 provided on the front face side of the pump body, a pressure-sensitive conductive layer 11 provided on the rear face of the first electrode 10, and a second electrode 12 provided spaced from the pressure-sensitive conductive layer 11. The resistance between the first electrode 10 and the second electrode 12 is higher than a few tens $M\Omega$ when the pressure-sensitive conductive layer 11 is apart from the second electrode 12, as shown in FIG. 9A; however, when the pressure-sensitive conductive layer 11 is pressed against the second electrode 12 at a pressure more than a specified pressure $P_0$ ($P_0=2$ Pa, for example), as shown in FIG. 9B, the resistance is lowered to a few $\Omega$ or less. FIG. 10 illustrates this electrical characteristic of the pressure sensor 6.

FIGS. 8A and 8B show a properly loaded state and a misloaded state of the IV tube 1, respectively. When the IV tube 1 is properly loaded to be located on the fluid propelling portion 2, as shown in FIG. 8A, closing of the door 5 will not cause a pressure to be applied to the pressure sensors 6. Therefore, the resulting resistance value will be more than a few tens $M\Omega$. On the other hand, when the IV tube 1 is misloaded so as to be displaced away from the fluid propelling portion 2 onto the pressure sensor 6 on one side thereof, as shown in FIG. 8B, closing of the door 5 will cause the door 5 to press the IV tube 1 such that a pressure higher than the specified pressure $P_0$ will be applied to the pressure sensor 6. The resulting resistance value will be a few $\Omega$ or less.

Accordingly, it can be detected whether or not the IV tube 1 is properly loaded, by measuring the resistances of the pressure sensors 6. Moreover, when an misloaded IV tube 1 is detected, operation of the fluid propelling portion 2 is prohibited so that no danger will arise to the patient.

However, with the conventional pressure sensors 6 as described above, the resistance value will read more than a few tens $M\Omega$ in either case where no force is encountered and the pressure-sensitive conductive layer 11 is apart from the second electrode 12, as in FIG. 9A, or where the pressure sensors 6 have been thrown into an inoperative state such as a damaged or unpowered state. This makes it impossible to differentiate between the properly loaded state of the IV tube 1 and the inoperative state of the pressure sensor 6. The result is that even if the IV tube 1 is misloaded, the inoperative state of the pressure sensors 6 would lead to a misdecision as proper loading, which would be of great danger to the patient.

SUMMARY OF THE INVENTION

The present invention has been developed with a view to substantially solving the above described disadvantage and has for its essential object to provide a peristaltic pumping apparatus which incorporates a pressure sensor that allows the differentiation between a properly loaded state of an IV tube and an inoperative state of a pressure sensor, the apparatus thereby being free from misdeciding a misloaded IV tube as properly loaded.

In order to achieve the aforementioned object, the present invention improves on a peristaltic pumping apparatus which has a body having a wall portion and a door for allowing access to the wall portion in its open position and impeding access to the wall portion in its closed position, a propelling means provided at the wall portion for propelling a fluid contained in a tube placed on the propelling means with a peristaltic pumping action when said door is closed, and a misloaded-tube detecting means.

A peristaltic pumping apparatus of the present invention has a misloaded-tube detecting means which comprises:

(a) a sensing means provided in the vicinity of a propelling means for sensing a pressure applied to the sensing means, and including a variable resistive element whose resistance varies in accordance with a magnitude of the applied pressure and a resistor connected in parallel with the variable resistive element and having a resistance of a predetermined value;

(b) a comparing means for receiving output from the sensing means and comparing a resistance of the sensing means with the resistance of the resistor and with a specified value which is smaller than the resistance of the resistor; and (c) a judging means for making a decision based on comparison results as to whether the tube is properly loaded or misloaded or whether the sensing means is in an inoperative state such as a damaged or unpowered state.

In an embodiment of the present invention, the sensing means comprises first and second electrodes spaced from each other; a pressure-resistive conductive element attached to one of the first and second electrodes so as to be located between the first and second electrodes in such a manner that the pressure-sensitive conductive element is apart from the other of the first and second electrodes when no pressure is applied to the sensing means and that the pressure-sensitive conductive element is forced against the second electrode when a pressure is applied to the sensing means, the pressure-resistive conductive element serving as the variable resistive element; and a resistor connected to the first and second electrodes.

The judging means decides as follows:

(i) the sensing means is in the inoperative state when the resistance of the sensing means is larger than the resistance of the resistor;

(ii) the tube is properly loaded on the propelling means when the resistance of the sensing means is between the resistance of the resistor and the specified value; and (iii) the tube is misloaded when the resistance of the sensing means is smaller than the specified value.

As obvious from above, according to the present invention, differentiation can be made between a state that the tube is loaded in a proper position and a state that the sensing means is in an operative state because of being damaged or unpowered. Accordingly, in the case of misloading of the tube, even if the sensing means is out of operation, the misloading will never be misrecognized as proper loading, so that a lack of administration of a medical agent to a patient can be prevented.

Preferably, the apparatus further comprises a controlling means for controlling operation of the propelling means based on the decision made by the judging means so that the propelling means is allowed to operate only when the tube is properly loaded and that the propelling means is prohibited from operating both when the sensing means is in the inoperative state and when the tube is misloaded.

Preferably, the apparatus may also have an alarm means for raising an alarm in response to output from the judging means indicating that the sensing means is in the inoperative state or that the tube is misloaded.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIGS. 8A and 8B show a properly loaded state and a misloaded state of an IV tube, respectively;

DETAILED DESCRIPTION OF THE PREFERRED EMBODIMENTS

The present invention is now described in more detail, referring to an embodiment as illustrated in the accompanying drawings.

Figure 1A:
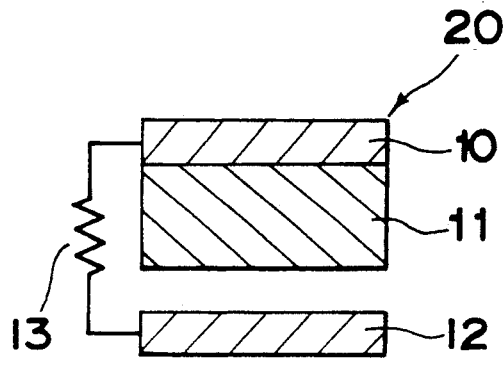
FIGS. 1A and 1B are cross-sectional views showing a pressure sensor according to the present invention in different operational states, respectively.
Figure 1B:
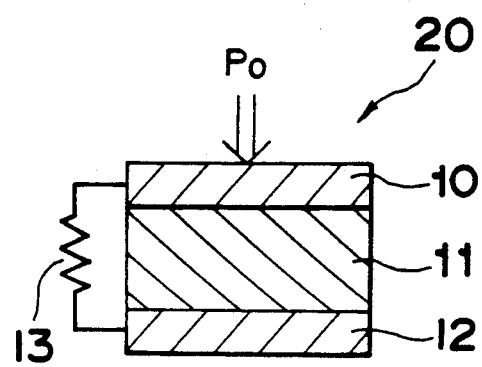
Figure 7:
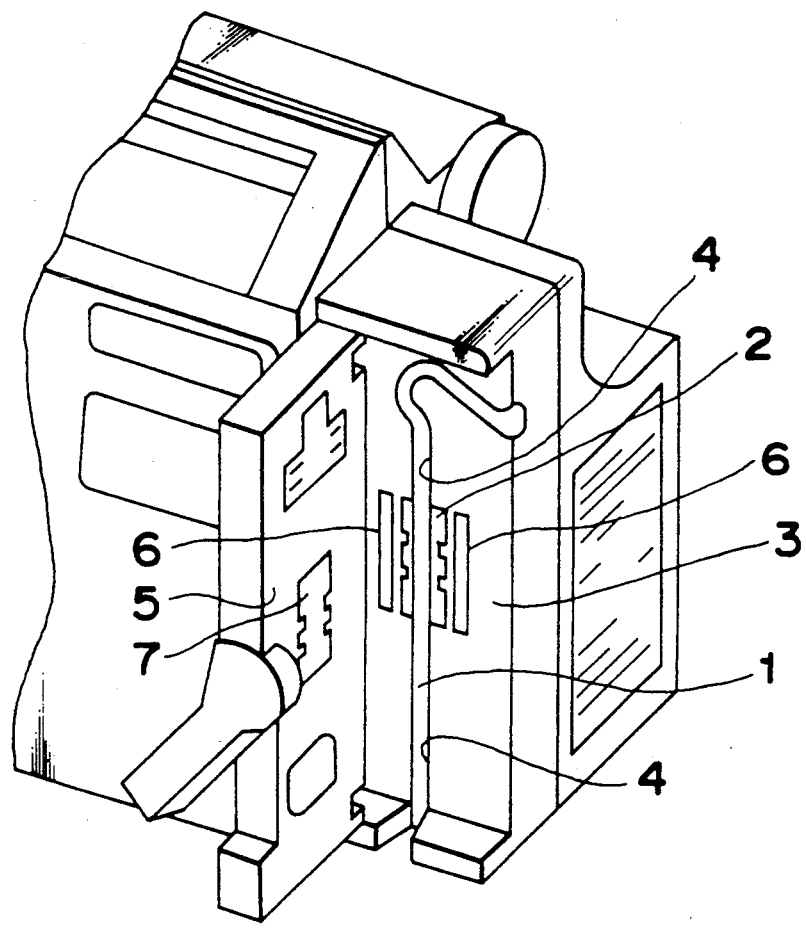
FIG. 7 is a perspective view showing a state in which the door of a peristaltic pumping apparatus is opened.
Figure 9A:
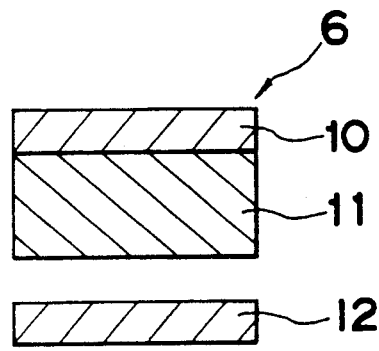
FIGS. 9A and 9B are cross sectional views showing a conventional pressure sensor in different operational states, respectively.
Figure 9B:
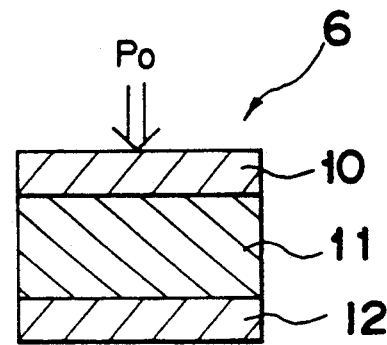
Figure 10:
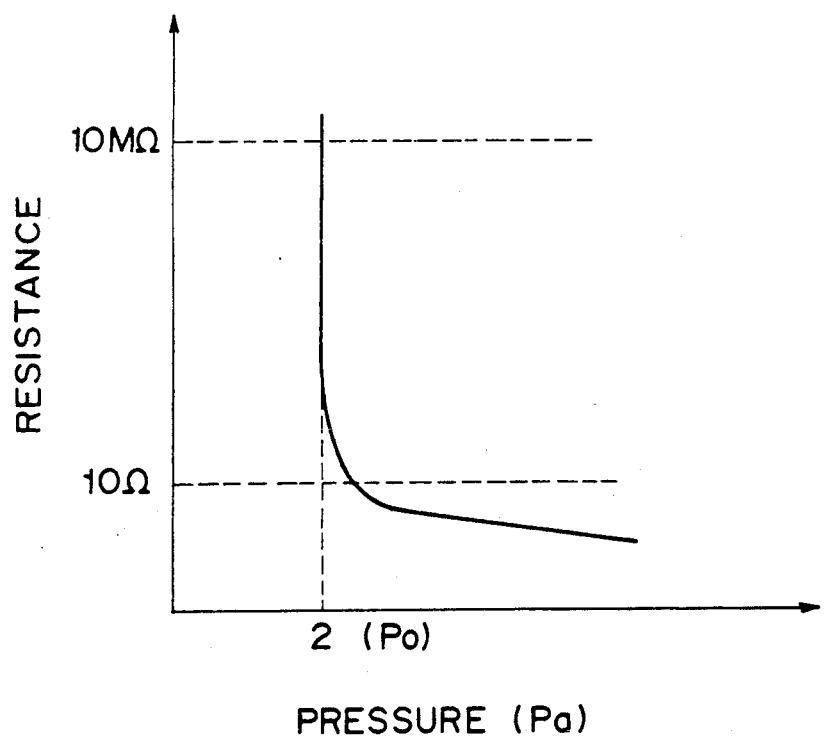
FIG. 10 shows an electrical characteristic curve of the conventional pressure sensors.

A peristaltic pumping apparatus of the present embodiment has an appearance similar to that of the conventional apparatus shown in FIG. 7. This apparatus incorporates pressure sensors 20 having the structure as shown in FIGS. 1A and 1B. Each pressure sensor 20 incorporates the first and second electrodes 10 and 12 and pressure-sensitive conductive layer 11 of the conventional pressure sensor 6 shown in FIGS. 9A and 9B.

Figure 2:
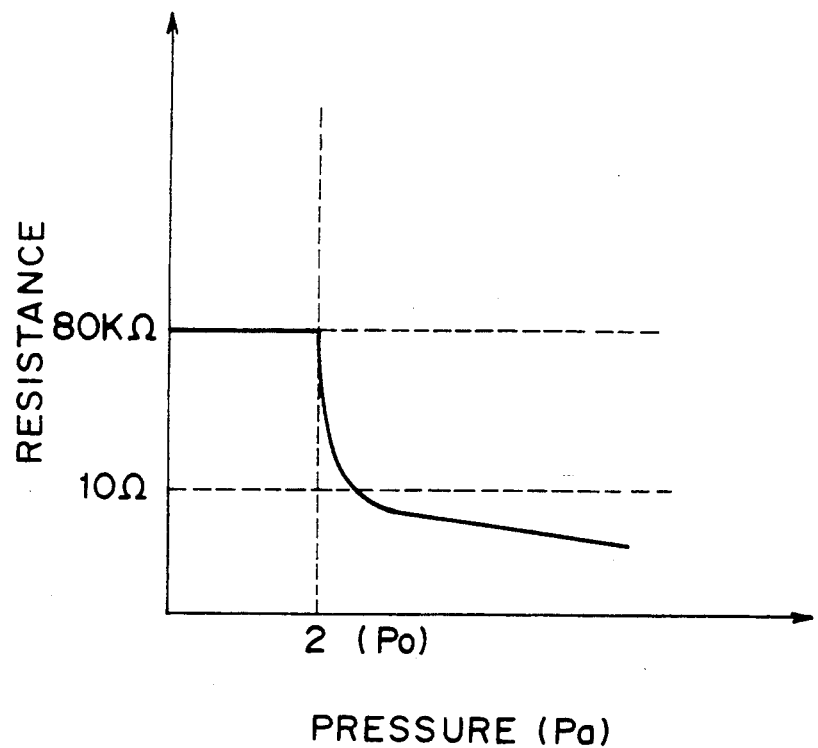
FIG. 2 shows an electrical characteristic curve of the pressure sensor of FIGS. 1A and 1B.

The first electrode 10 and the second electrode 12 are connected via a resistor 13 having a resistance of a few tens KΩ (in this embodiment, 80 KΩ is used). As a result, the pressure sensors 20 each present an electrical characteristic as shown in FIG. 2. That is, in the state in which no pressure is applied to the first electrode 10, as in FIG. 1A, a resistance between the first electrode 10 and the second electrode 12 (this resistance is hereinafter referred to as interelectrode resistance) is approximately equal to that of the resistor 13 (80 K$\Omega$). If the pressure acting on the first electrode 10 is less than a specified pressure $P_0$ ($P_0 = 2$ Pa in this embodiment), the pressure-sensitive conductive layer 11 will not be urged against the second electrode 12, so that the interelectrode resistance will remain to be approx. 80 K$\Omega$. When a pressure larger than the specified pressure $P_0$ is applied to the first electrode 10, bringing the pressure sensor 20 into the state of FIG. 1B wherein the pressure-sensitive conductive layer 11 is pressed against the second electrode 12, the resistance of the pressure-sensitive conductive layer 11 will decrease to a few $\Omega$ or less, and the interelectrode resistance will also become a few $\Omega$ or less.

Figure 3:
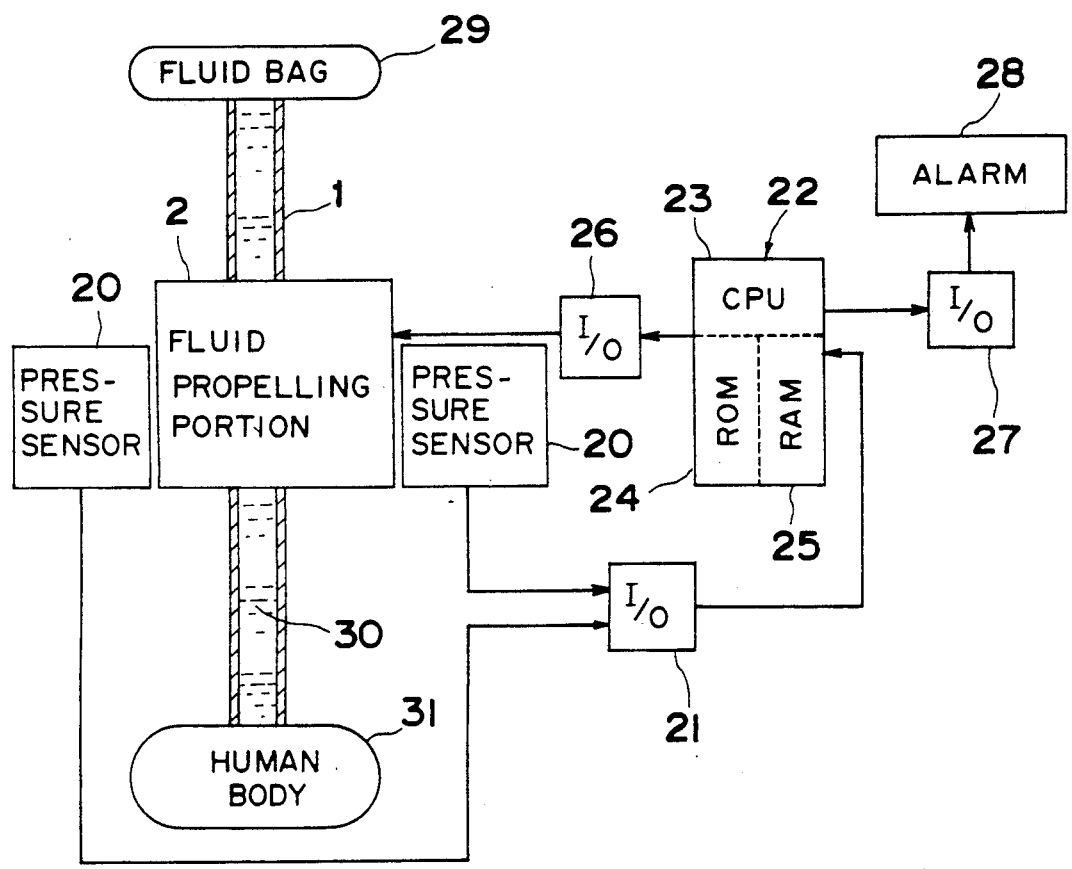
FIG. 3 is a block diagram of a peristaltic pumping apparatus according to an embodiment of the present invention which incorporates the pressure sensor shown in FIGS. 1A and 1B.

As shown in FIG. 3, the pressure sensors 20 are connected via an I/O (Input/Output) circuit 21 to a microcomputer 22. This microcomputer 22 is equipped with a CPU 23, a ROM 24, and a RAM 25. The CPU 23 has a function of measuring the interelectrode resistance of each pressure sensor 20, a function of deciding from the measured interelectrode resistance value whether an IV tube 1 is properly loaded or misloaded or whether the pressure sensor 20 is inoperative because of being damaged or unpowered, a function of controlling a fluid propelling portion 2 via an I/O 26 on the basis of the decision result, and a function of informing an alarm 28 via an I/O 27 that the IV tube 1 is misloaded or that a pressure sensor 20 is inoperative.

The fluid propelling portion 2 includes a plurality of reciprocating pressure fingers which are associated with a pressure plate 7 carried by the door 5 (see FIG. 7) to propel a fluid or solution 30 within the IV tube 1, which solution has been fed from a fluid bag 29, toward a human body 31 by making the IV tube 1 repeatedly urged against the pressure plate 7 to thereby cause a peristaltic motion to the IV tube 1, under control of the CPU 23. The alarm 28, receiving a signal from the CPU 23, gives an alarm indicative of either misloading of the IV tube or the pressure sensor being in an inoperative state (hereinbelow referred to as "misloaded-tube alarm" and "sensor-error alarm" respectively).

Figure 4:
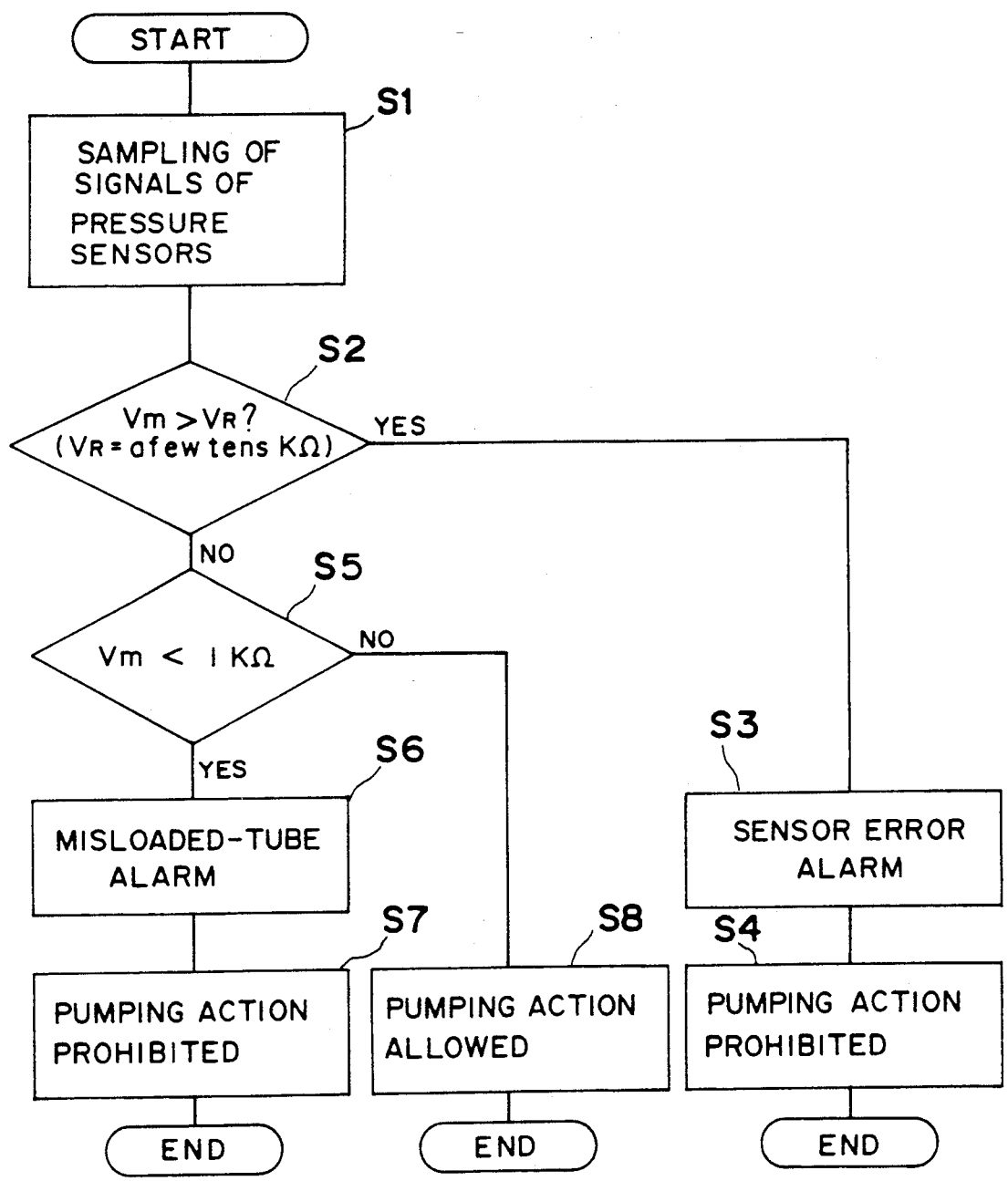
FIG. 4 is a flowchart showing the operation of the peristaltic pumping apparatus of FIG. 3.

Next, the operation of the CPU 23 is explained referring to the flowchart of FIG. 4.

First, at step S1, a signal of each pressure sensor 20 is sampled for the interelectrode resistance value to be measured. Next, the program goes to step S2, at which it is decided whether or not the measured interelectrode resistance value $V_M$ is larger than the resistance value $V_R$ (80 K$\Omega$) of the resistor 13. Then if the measured interelectrode resistance value $V_M$ is larger than the resistance value $V_R$ of the resistor 13, the pressure sensor 20 is decided to be in an inoperative state. In this case, at step S3 the alarm 28 is controlled to give the sensor-error alarm and moreover at step S4 the fluid propelling portion 2 is prohibited from executing the peristaltic pumping action. On the other hand, if the measured interelectrode resistance value $V_M$ is equal to or smaller than the resistance value $V_R$ of the resistor 13, the program goes to step S5, at which it is decided whether or not the measured interelectrode resistance value $V_M$ is less than 1 K$\Omega$. Then if the measured interelectrode resistance value $V_M$ is less than 1 K$\Omega$, the IV tube 1 is decided to have been misloaded, in which case at step S6 the alarm 28 is controlled to give the misloaded-tube alarm and moreover at step S7 the fluid propelling portion 2 is prohibited from executing the peristaltic pumping action. If the measured interelectrode resistance value $V_M$ is not less than 1 K$\Omega$, the IV tube 1 is decided to have been properly loaded, in which case at step S8 the fluid operating portion 2 is allowed to execute the peristaltic pumping action.

As described above, since differentiation can be made between a state in which the IV tube is properly loaded and a state in which either pressure sensor 20 is in the inoperative state such as a damaged or unpowered state, the IV tube 1 will never be misdecided as having been properly loaded when actually misloaded, even if the pressure sensors 20 are in an inoperative state. Thus, the apparatus of the present embodiment is safe to the patient.

Although the pressure-sensitive conductive layer 11 is provided on the first electrode 10 in the present embodiment, it may also be provided on the second electrode 12.

Figure 5:
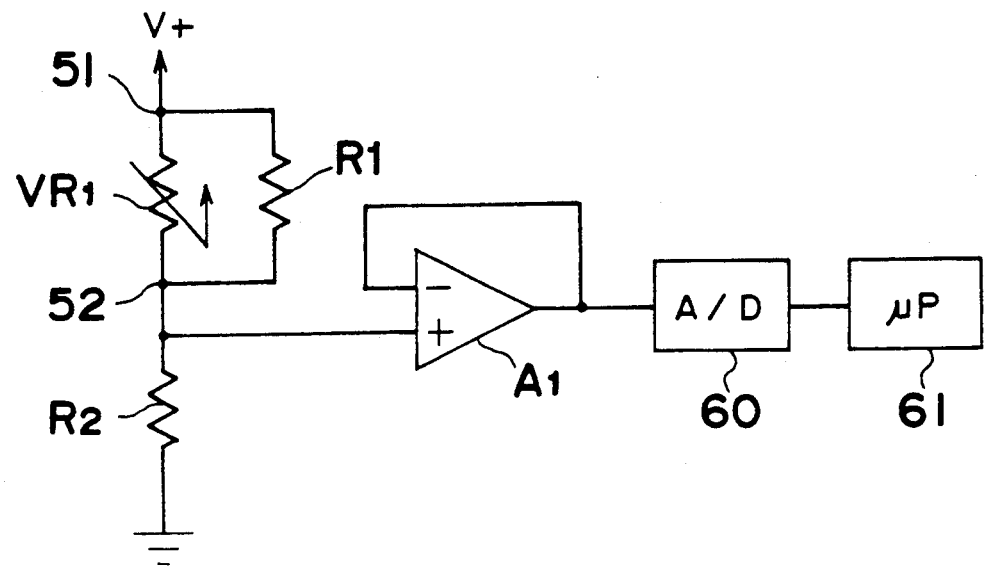
FIG. 5 is a circuit diagram of a detection circuit using a pressure sensor circuit equivalent to the pressure sensor of FIGS. 1A and 1B.
Figure 6:
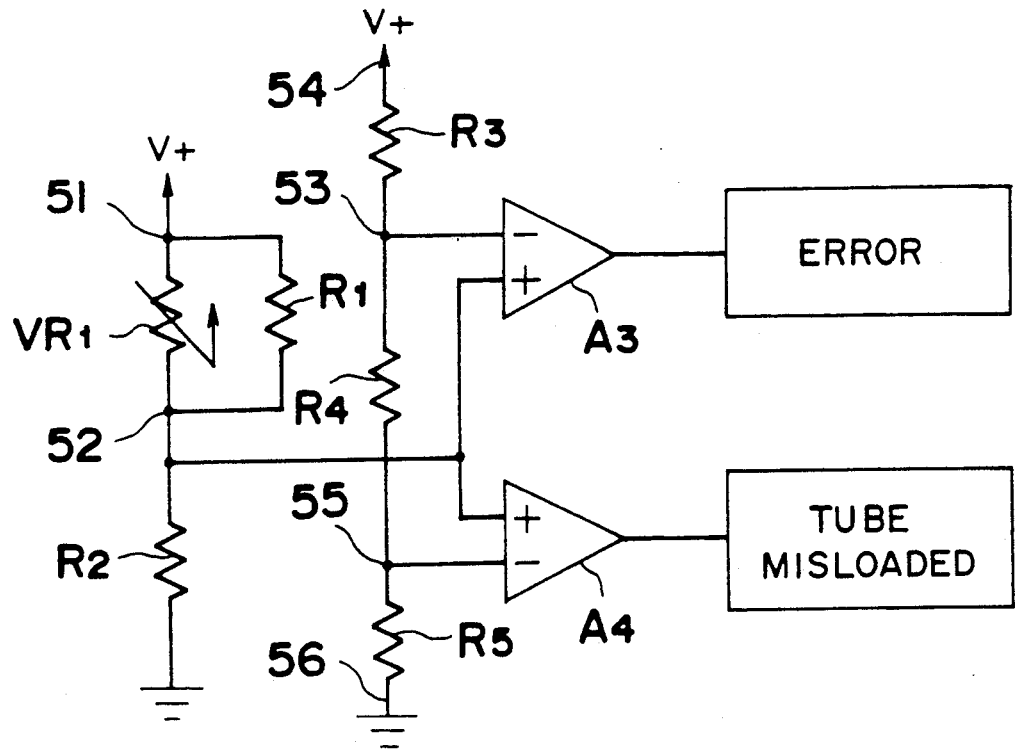
FIG. 6 is a circuit diagram of a variant of the detection circuit of FIG. 5.

Also, although in the present embodiment the CPU 23 measures the resistance values of the pressure sensors 20 and decides based on the measured values whether or not the tube has been properly loaded or misloaded or whether either of the pressure sensors is in an inoperative state, such an electronic circuit as shown in FIG. 5 or 6 may be also used to make the decision.

Referring to FIG. 5, the electronic circuit has a pressure-sensitive resistor $VR_1$ which is a variable resistor. This pressure-sensitive resistor $VR_1$ is connected in parallel with a resistor $R_1$ so that a circuit construction equivalent to that of the pressure sensor 20 is obtained. One junction 51 of the pressure-sensitive resistor $VR_1$ and the resistor $R_1$ is connected to a power source $V+$. The other junction 52 of the pressure-sensitive resistor $VR_1$ and the resistor $R_1$ is connected via a second resistor $R_2$ to ground.

The junction 52 of the parallel resistors $VR_1$ and $R_1$ is also connected to a non-inverting input terminal (+) of an operational amplifier $A_1$. The output of the operational amplifier $A_1$ is directly fed back to its inverting input terminal (−) to set gain at 1.

The output of the operational amplifier $A_1$ is also input into an A/D (analog-to-digital) converter 60. The A/D converter 60 converts the received analog signal to a digital output for subsequent input into a monitoring microprocessor 61.

The resistors $R_1$, $R_2$, $VR_1$ form a voltage divider. The voltage divider provides three operative state outputs. A first output state occurs when the electronic circuit is operating properly and no force acts on the pressure-sensitive variable resistor $VR_1$. This occurs either before the IV tube is loaded or when the IV tube has been properly loaded. In this state, the pressure-sensitive variable resistor $VR_1$ has an extremely large resistance value which in effect is equivalent to an open state. Accordingly, the resistors $R_1$ and $R_2$ form a voltage divider to output a predetermined voltage.

In a second state, the electronic circuit is damaged, inoperable, or not powered. In this state, no voltage will be outputted.

In a third state, the IV tube 1 is misloaded and exerts a force on the pressure-sensitive variable resistor $VR_1$. Because the door of the apparatus has been forced closed in an attempt to force operation, this force is significant. With this force exerted, the resistance of the pressure-sensitive resistor $VR_1$ decreases to a relatively small one. This preset resistance cooperates with the resistor $R_2$ so as to form a voltage divider for producing a predetermined voltage.

The resistances of the force-activated variable resistor $VR_1$, resistor $R_1$, and resistor $R_2$ are preset to allow differentiation among the first, second and third states.

The output signal is then buffered by the operational amplifier $A_1$ with a gain of 1 and subsequently a signal is provided to the A/D converter 60. The output of the A/D converter 60 is input into the microprocessor 61. The microprocessor is preset to "read" the various signals and interpret which state the misloaded tube detection circuit is in.

FIG. 6 diagrams alternative preferred electronic circuit. Also in this case, the pressure-sensitive variable resistor $VR_1$ is provided in parallel with the resistor $R_1$. One junction 51 of the pressure-sensitive variable resistor $VR_1$ and the resistor $R_1$ is connected to a power source $V+$. The second junction 52 of the pressure-sensitive variable resistor $VR_1$ and the resistor $R_1$ is connected to ground via the resistor $R_2$.

The junction 52 of the parallel resistors $VR_1$ and $R_1$ is also connected to non-inverting input terminals (+) of two operational amplifier $A_3$ and $A_4$. The inverting input terminal (−) of the operational amplifier $A_3$ is connected to a junction 53 of two series resistors $R_3$ and $R_4$. The other junction or connecting point 54 of the resistor $R_3$ is connected to a power source $V+$. The inverting input terminal (−) of the operational amplifier $A_4$ is connected to a junction 55 of the resistor $R_4$ and a series resistor $R_5$.

A connecting point 56 of the resistor $R_5$ is connected to ground.

Thus, the pressure-sensitive variable resistor $VR_1$, resistor $R_1$, and resistor $R_2$ will operate in the manner described above. The series resistors $R_3$, $R_4$, and $R_5$ are selected to form a preset voltage divider for setting levels for tube misloading and circuit error detection. If a tube misloading is read, the operational amplifier $A_4$ outputs a high level signal, while if a circuit error is read, the operational amplifier $A_3$ outputs a high level signal. As can be readily appreciated by one skilled in the art, the outputs of the operational amplifiers $A_3$ and $A_4$ can be used to signal the state of the tube.

Although the present invention contemplates use of any pressure-sensitive or reactive resistor element, the present embodiments are designed to use a pressure-sensitive resistor element having a resistance value which is inversely related to the pressure or force applied to the element. An appropriate pressure-sensitive resistor element is available from Interlink Electronics of Santa Barbara, Calif. Of course, other resistive sensors are contemplated as within the scope of the present invention. Furthermore, use of other electronic sensors such as a capacitive sensor or a thin membrane type switch are also contemplated.

It should be understood that various changes and modifications to the preferred embodiments will be apparent to those skilled in the art. For example, while the present invention has been described in conjunction with the peristaltic pump having pressure fingers, the principles of the present invention can also apply to a rotary-type peristaltic pump. Such changes and modifications can be made without departing from the spirit and scope of the present invention without diminishing its intended advantages. It is therefore, intended that such changes and modifications be covered by the appended claims.

What is claimed is:

1. A peristaltic pumping apparatus comprising:
   a body having a wall portion and a door for allowing access to said wall portion in its open position and impeding access to said wall portion in its closed position;
   a propelling means provided at said wall portion for propelling a fluid contained in a tube placed on said propelling means with a peristaltic pumping action when said door is closed;
   a detecting means for detecting misloading of said tube, said detecting means having:
   (a) a sensing means provided in the vicinity of said propelling means for sensing a pressure applied to said sensing means, and including a variable resistive element whose resistance varies in accordance with a magnitude of the applied pressure and a resistor connected in parallel with said variable resistive element and having a resistance of a predetermined value;
   (b) a comparing means for receiving output from said sensing means and comparing a resistance of said sensing means with the resistance of said resistor and with a specified value which is smaller than the resistance of said resistor; and
   (c) a judging means for making a decision based on comparison results as to whether said tube is properly loaded or misloaded or whether said sensing means is in an inoperative state such as a damaged or unpowered state.

2. The apparatus of claim 1, wherein said judging means decides that:
   (i) said sensing means is in the inoperative state when the resistance of said sensing means is larger than the resistance of said resistor;
   (ii) said tube is properly loaded on said propelling means when the resistance of said sensing means is between the resistance of said resistor and said specified value; and
   (iii) said tube is misloaded when the resistance of said sensing means is smaller than said specified value.

3. The apparatus of claim 1, further comprising a controlling means for controlling operation of said propelling means based on the decision made by said judging means so that said propelling means is allowed to operate only when said tube is properly loaded and that said propelling means is prohibited from operating both when said sensing means is in the inoperative state and when said tube is misloaded.

4. The apparatus of claim 1, further comprising an alarm means for raising an alarm in response to output from said judging means indicating that said sensing means is in the inoperative state or that said tube is misloaded.

5. The apparatus of claim 1, wherein said sensing means comprises:
   first and second electrodes spaced from each other;
   a pressure-resistive conductive element attached to one of said first and second electrodes so as to be located between said first and second electrodes in such a manner that said pressure-sensitive conductive element is apart from the other of said first and second electrodes when no pressure is applied to said sensing means and that said pressure-sensitive conductive element is forced against said second electrode when a pressure is applied to said sensing means, said pressure-resistive conductive element serving as said variable resistive element; and
   a resistor connected to said first and second electrodes.

* * * * *

UNITED STATES PATENT AND TRADEMARK OFFICE
CERTIFICATE OF CORRECTION

PATENT NO. : 5,312,334

DATED : May 17, 1994

INVENTOR(S) : K. Hara, et al.

It is certified that error appears in the above-identified patent and that said Letters Patent is hereby corrected as shown below:

Cover page to Patent, item [73], add:

--Baxter International Incorporated
One Baxter Parkway
Deerfield, Illinois 60015--

Signed and Sealed this

Sixth Day of December, 1994

Attest:

BRUCE LEHMAN

*Attesting Officer*     *Commissioner of Patents and Trademarks*